United States Patent [19]  [11] Patent Number: 4,621,735
Coon et al.  [45] Date of Patent: Nov. 11, 1986

[54] COVER FOR SURGICAL LIGHT HANDLE AND TOUCH PANEL

[75] Inventors: Dennis C. Coon; Michael A. Narusewicz; Ward L. Sanders, all of Erie, Pa.

[73] Assignee: American Sterilizer Company, Erie, Pa.

[21] Appl. No.: 705,972

[22] Filed: Feb. 27, 1985

[51] Int. Cl.⁴ .............................................. B65D 81/28
[52] U.S. Cl. .................................... 206/438; 206/363; 206/439; 206/470; 422/1; 422/40
[58] Field of Search ................. 422/40, 292, 297, 300; 206/205, 363, 438, 470, 525, 439; 220/200, 212, 287, 400; 235/145 R; 128/396; 604/905; 150/52 R; 350/585, 586, 587

[56] References Cited

U.S. PATENT DOCUMENTS 3,054,679 9/1962 Bradford .
3,381,813 5/1968 Coanda et al. .
3,561,668 2/1971 Bergstrom .
3,685,720 8/1972 Brady .............................. 206/438 X
3,720,250 3/1973 Goldberg et al. .
3,749,271 7/1973 Ellis, Jr. et al. .
3,862,654 1/1975 Goldberg et al. .
4,075,465 2/1978 Funk et al. ....................... 235/145 R
4,266,663 5/1981 Geraci ........................... 150/52 R X Primary Examiner—Barry S. Richman
Assistant Examiner—Jill Johnston
Attorney, Agent, or Firm—Robert D. Yeager; Christine R. Ethridge; Edward L. Pencoske

[57] ABSTRACT

An assembly for permitting a sterile person to control adjustable equipment in a sterile field without contamination to the person or the field. The assembly includes a cover having two halves which can be folded together over the handle of the equipment in a closed position to isolate the handle from the sterile field. A flap on the cover isolates a control panel on the equipment from the sterile field. The assembly also includes a container in which the cover is sterilized and with which the cover is so applied to the handle following sterilization that the container provides a barrier against contamination of the exterior of the cover during such application. The container is structured to maintain the cover in a partially closed position and is adapted to be so deformed that the container can move the cover from the partially closed position to a closed position around the handle.

5 Claims, 12 Drawing Figures

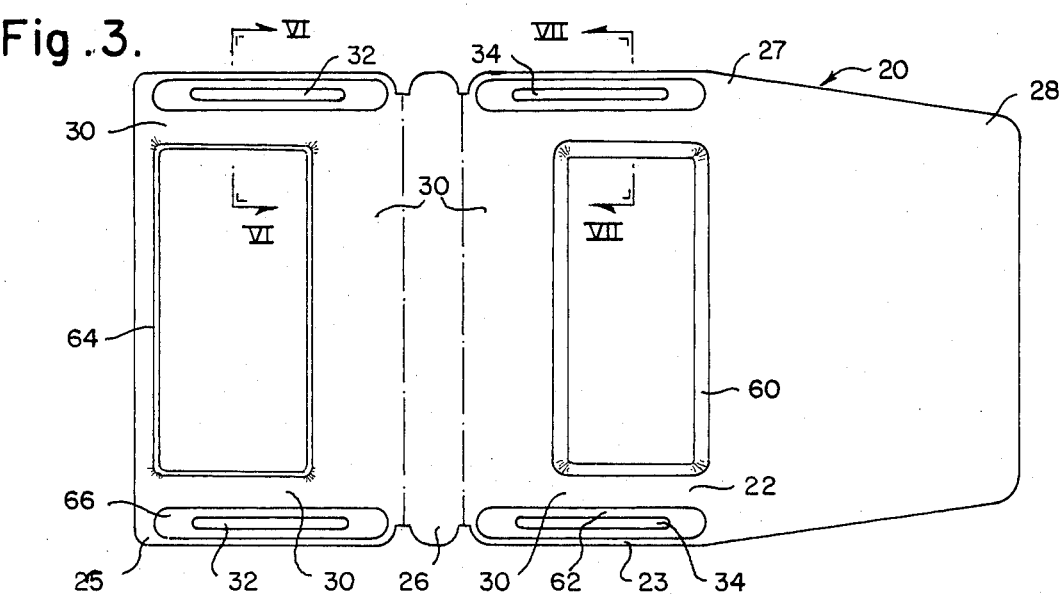
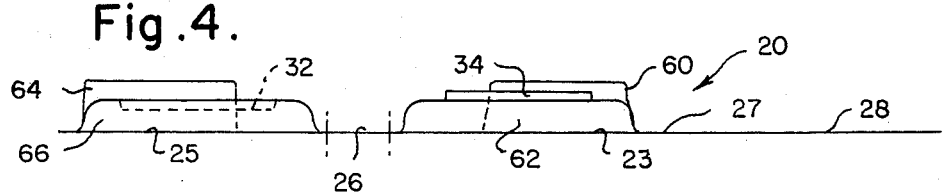
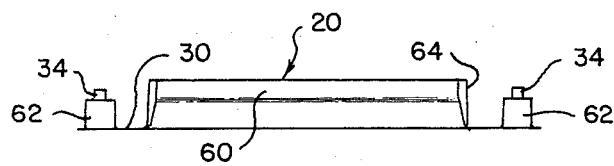
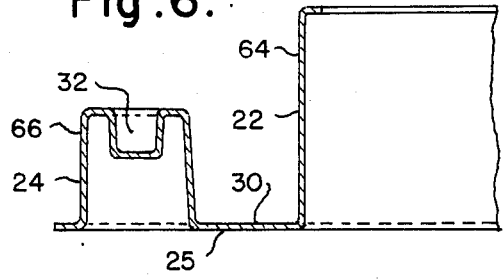
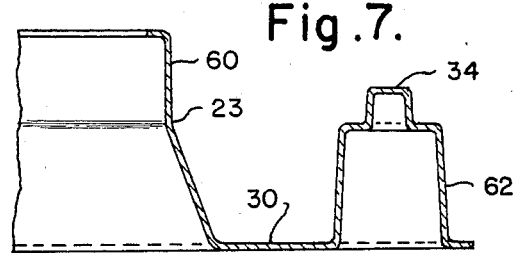
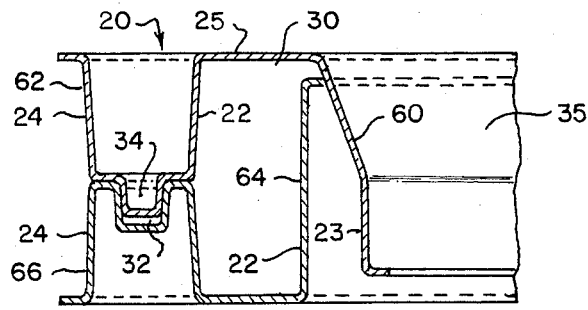

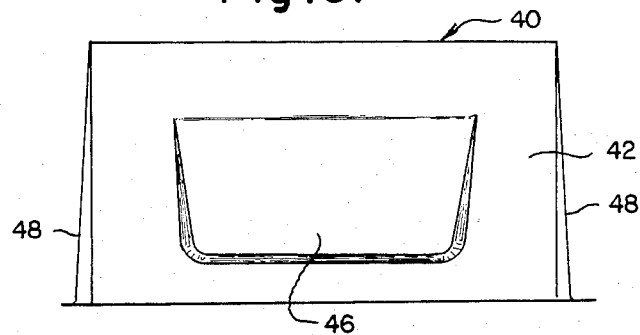
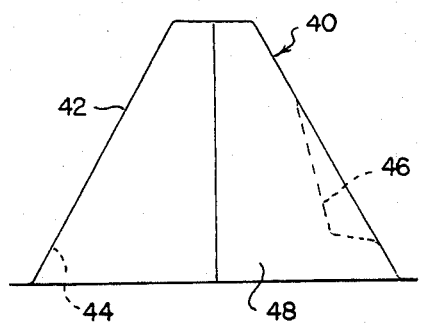
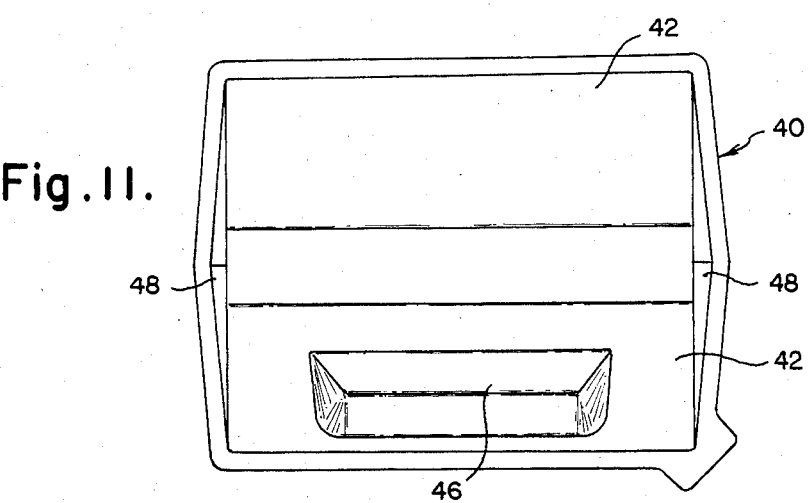
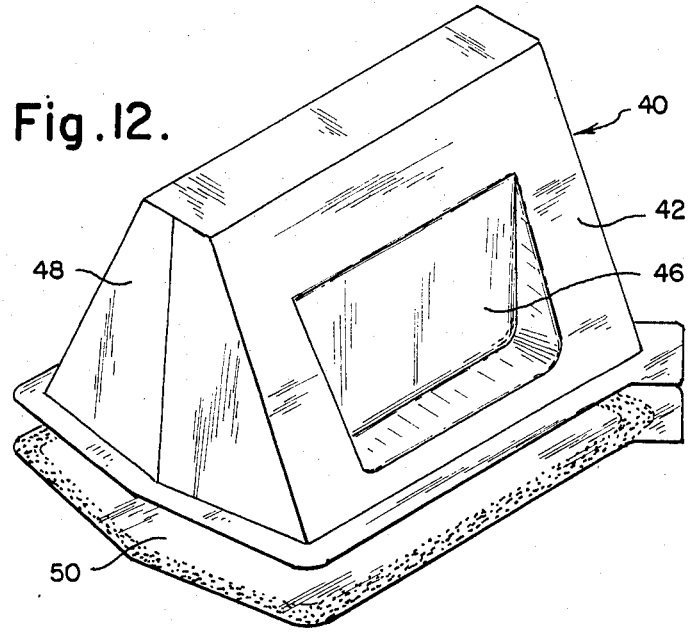

COVER FOR SURGICAL LIGHT HANDLE AND TOUCH PANEL

BACKGROUND OF THE INVENTION

1. Field of the Invention

The present invention relates to sterile covers for the handles of adjustable apparatus for use in a sterile field.

2. Description of the Prior Art

To curb the rising costs of health care, small ambulatory care centers are performing many of the more routine services traditionally performed in hospitals. Many of those services, such as outpatient surgery, must be performed with the aid of traditional equipment under sterile conditions. In an ambulatory care facility the physician performing the service is often assisted by only one individual, and both the physician and the assistant must be sterile throughout the procedure. Therefore, unlike hospital surgeons having a large support staff to operate the equipment outside of the sterile field during a procedure, the ambulatory care physician or the assistant must operate any necessary equipment themselves and without the risk of contaminating themselves or the sterile field.

The current practice is to operate the controls of equipment, for example, pressing a button or switch on the control panel of a surgical light to adjust the light intensity, by means of a sterile rod. The sterile physician or assistant holds one end of the sterile rod and presses a control button with the other end. A similar procedure can be used to adjust the position of the surgical light. While the operation of equipment by means of such sterile rods is effective, it is obviously awkward.

Sterilization containers are well known in the art and sterile covers for use with surgical light handles are commercially available. The sterile covers, however, must be applied to the light handle by a sterile person. The covers are made of elastomeric materials and are currently packaged in a manner which too often deforms the shape of the cover. The deformed covers are difficult to apply with the required aseptic technique and often do not entirely cover the handle. Thus, the cover may become contaminated, or when the sterile person touches the cover, he or she may inadvertently touch the exposed portion of the nonsterile light handle. The known sterile covers are often inadequate.

There is a need, therefore, for a means which permits a sterile person to operate and/or adjust nonsterile equipment in a sterile field without the risk of contamination. It is an object of the present invention to provide a sterile cover to isolate the adjustment handles and control panels of equipment used in sterile fields and further, to provide a container in which the cover is sterilized and stored, and with which the cover can be applied to the handle without contaminating the cover.

SUMMARY OF THE INVENTION

The present invention provides a means for covering the handle and control panel of nonsterile adjustable equipment which permits a sterile person to operate and adjust the equipment in a sterile field without the risk of contamination.

The means of the present invention is an assembly which includes a thermoformed cover adapted to isolate the handle and the control panel from the sterile field, and a container in which the cover is sterilized and with which the cover is adapted to be so applied to the handle following sterilization that the container provides a barrier against contamination of the exterior of the cover during such application.

The cover has a fold section dividing the cover into a first half and a second half, the cover being adapted to bend along the fold section to permit the first and second halves to be so joined that the cover assumes a closed position in which the joined halves conform generally to the shape of the handle and define an interior and an exterior. There are means formed in the halves to hold the halves in the closed position. A flap is attached to one end of the first half and is adapted to assume a position in which the flap isolates the control panel when the cover is in the closed position.

The cover preferably includes as the holding means, at least one rib on the first half and at least one channel on the second half. The channel is adapted to receive the rib in a locking engagement to hold the halves in the closed position.

The container is so structured that the cover is maintained within the container in a partially closed position. The container is adapted to be so deformed that the container moves the cover from the partially closed position to the closed position.

The container preferably includes an indented portion to facilitate moving the cover from the partially closed to the closed position.

The container is made of a material which is impervious to microorganisms and which has at least a portion thereof that is permeable to a sterilant. The container also includes removable means for sealing the cover within the container during sterilization and storage.

The removable sealing means is preferably a lid which includes the sterilant permeable portion and which covers an opening in the container.

BRIEF DESCRIPTION OF THE DRAWINGS

The following detailed description of the preferred embodiment can be better understood if reference is made to the attached drawings in which:

FIG. 3 is a top plan view of the cover of FIG. 2 in a fully open position;

FIG. 4 is a side view of the cover of FIG. 3;

FIG. 5 is a front end view of the cover of FIG. 3;

FIG. 6 is a partial section view through the line VI—VI of FIG. 3;

FIG. 7 is a partial section view through the line VII—VII of FIG. 3;

FIG. 8 is a partial section view of the cover in a closed position;

FIG. 9 is a side elevation view of the front of the container of FIG. 2;

FIG. 10 is an end view of the container of FIG. 9;

FIG. 11 is a top plan view of the container of FIG. 9; and

FIG. 12 is an isometric view of the container separated from the removable lid.

DETAILED DESCRIPTION OF THE PREFERRED EMBODIMENTS

Figure 1:
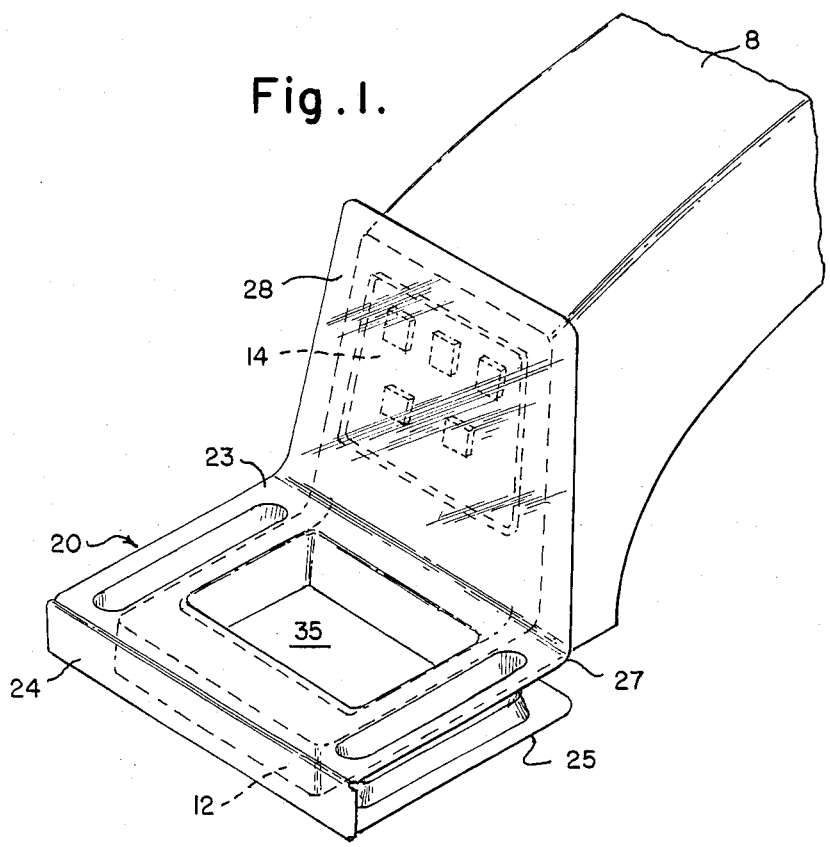
FIG. 1 is an isometric view of the preferred embodiment of the cover of the present invention covering the handle and control panel of adjustable equipment.

FIGS. 1 through 12 illustrate the preferred embodiment of the assembly 10 of the present invention. The assembly 10 provides a means for permitting a sterile person to operate nonsterile adjustable equipment in a sterile field without the risk of contamination to the person or the field. For purposes of description, the adjustable equipment shown in FIG. 1 is an overhead surgical light 8 having a generally U-shaped handle 12 and a control panel 14 adjacent to the handle 12. The position of the surgical light 8 can be adjusted by moving the handle 12. The control panel 14 may include, for example, power and intensity push button or pressure sensitive controls. The control panel 14 is positioned adjacent to the handle 12 so that a person can operate the controls and adjust the position of the light simultaneously with one hand.

The assembly 10 includes a cover 20 and a container 40. Cover 20 can be sterilized and stored in container 40 until needed for use with surgical light 8. At that time, the container 40 is used to apply cover 20 to handle 12.

Cover 20 is a single molded structure configured to completely cover handle 12 and control panel 14. The cover 20 can be premolded by any suitable known means to conform to the shape of the handle it is intended to cover.

Referring to FIG. 3, cover 20 is in a fully open, flat position. The cover 20 includes an interior surface 22 and an exterior surface 24. A fold section 26 divides the cover 20 into a first, or top half 23 and a second, or bottom half 25. The terms "top" and "bottom" refer to the orientation of the halves, 23 and 25, on the handle 12 when the handle 12 lies in a generally horizontal plane. The cover 20 can be used on a handle in any orientation. Flap 28 is attached to end 27 of the top half 23. Flap 28 is adapted to cover control panel 14 to isolate control panel 14 from the sterile field.

Each half 23 and 25, includes a rectangular portion and two side portions which define recesses 30. Top half 23 has rectangular portion 60 and side portions 62. Bottom half 25 has rectangular portion 64 and side portions 66. Rectangular portion 60 fits within rectangular portion 64 when cover 20 is closed. Rectangular portion 64 and the interior of side portions 62 and 66 form walls around handle 12 and enclose handle 12 within recesses 30 when the halves are folded together along fold section 26 over the handle 12. When so folded, the cover 20 defines a space 35 and interior and exterior surfaces 22 and 24, respectively. The space 35 is formed between the interiors of the rectangular portions 60 and 64.

Bottom half 25 includes two channels 32 in side portions 66, each of which is adapted to receive a rib 34. The ribs 34 protrude from side portion 62 of top half 23 and are aligned to snap into the channels 32 of the bottom half 25 when the halves are folded together around handle 12. The ribs 34 and channels 32 thus provide a means of holding the cover 20 in a locking engagement on the handle 12 in a fully closed position.

Figure 2:
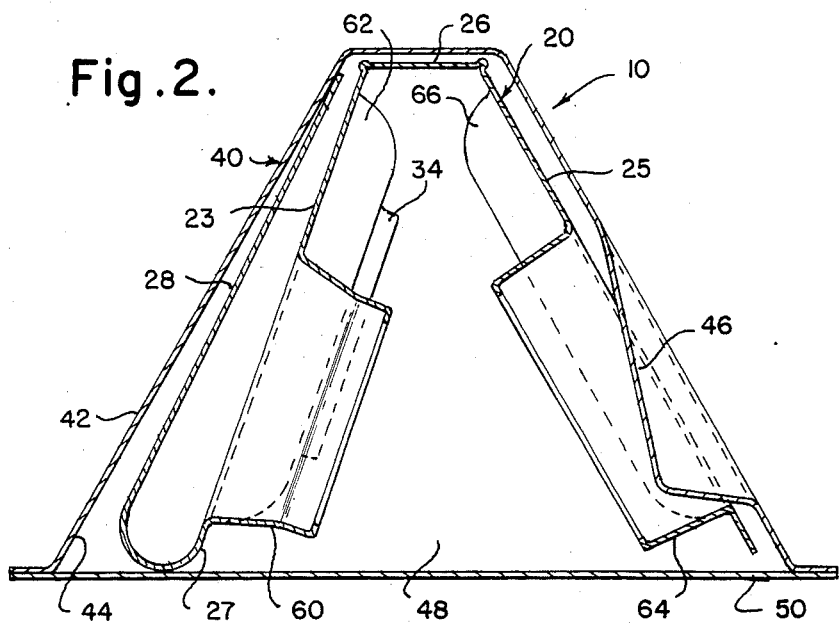
FIG. 2 is an end view of the preferred embodiment of the assembly of the present invention showing the cover in a partially closed position within the container.

The cover 20 is held within container 40 during sterilization and storage. Container 40 is preferably configured to permit cover 20 to be positioned therein in a partially closed position as shown in FIG. 2. Container 40 includes an exterior surface 42, an interior surface 44, and an indentation 46 on the exterior 42. The indentation 46 fits into the interior of rectangular portion 64 which helps to define the space 35 when the cover is fully closed. Container 40 also defines an opening 48 and includes means for sealing cover 20 within container 40 during sterilization and storage.

The means for sealing cover 20 within container 40 is preferably a lid 50 which is sealed along its periphery over opening 48 by any suitable known means, such as a heat or pressure sensitive adhesive. Container 40 is made of a thermoplastic material which is impervious to microorganisms and which has at least a portion thereof which is permeable to sterilants, such as steam, ethylene oxide or irradiation. The sterilant permeable portion, preferably lid 50, is made of breathable, surgical kraft paper, or any other suitable sterilant permeable material.

To use assembly 10, the premolded thermoformed cover 20 is placed by the manufacturer in container 40 so that, except for flap 28, most of the exterior surface 24 of cover 20 faces the interior surface 44 of container 40. The configuration of container 40 holds cover 20 in a partially closed position, as shown in FIG. 2, wherein the top half 23 is bent along fold section 26 in an acutely angular orientation relative to the bottom half 25. Flap 28 is bent back along end 27 of top half 23 between top half 23 and the interior surface 44 of container 40. Lid 50 seals the cover 20 within container 40.

Before use, the sealed assembly 10 is sterilized in any suitable sterilizer. Thereafter, the assembly 10 can be stored in a sterile state until needed or can be transported directly to the sterile field. Container 40 can then be used to apply cover 20 to handle 12.

To apply cover 20 to a handle 12, the lid 50 is peeled away to open container 40. A nonsterile person can apply the sterile cover 20 by holding the exterior surface 42 of container 40 in one hand, placing the fingers or thumb in indentation 46.

The opening 48 of container 40 and the angular orientation of the partially closed cover 20 are wide enough to be positioned around handle 12 in a manner that permits the recesses 30 of the top half 23 to be aligned on one side of handle 12 and the recesses 30 of the bottom half 25 to be aligned on the opposite side of handle 12. By squeezing the fingers and thumb of the hand together to press the opposing sides of container 40 together, the person applying cover 20 to handle 12 can join the bottom and top halves, 25 and 23, respectively, into a fully closed position surrounding handle 12. The ribs 34 snap into the channels 32 to lock the cover 20 in place.

When the container 40 is pulled away, the flap 28 springs up over the control panel 14. The cover 20 must be made so that the natural tendency of flap 28 is to assume a position necessary to cover the control panel 14.

The exterior surface 24 of cover 20 remains protected by container 40 during application of the cover 20, even by a nonsterile person, because the person applying the cover 20 need never touch it. The cover 20 provides a means of shielding a sterile field from the handle of nonsterile adjustable equipment. It also provides a sterile surface which can be grasped by a sterile person in the sterile field to adjust the position of the equipment and/or to operate the control panel 14.

The sterile person can press the appropriate button or pressure point by pressing the flap 28 against that button or point. Thus, flap 28 provides a barrier between the nonsterile control panel 14 and the sterile person operating it.

What is claimed is:

1. An assembly for enabling a nonsterile person to attach a sterile barrier to a handle and a control panel of nonsterile adjustable equipment located in a sterile field, said assembly comprising:

a sterile cover for isolating a handle and a control panel from a sterile field, said cover having a fold section dividing said cover into first and second halves, said cover being bendable along said fold section for permitting said cover to assume a closed position in which said halves conform generally to the shape of a handle, said cover having means carried by said first and second halves for holding said cover in said closed position, said cover further having a flap attached to one of said halves; and a container configured for housing said cover in a partially closed position while maintaining said flap in compression, said container being constructed of a deformable material which is impervious to microorganisms thereby maintaining said cover sterile and permitting, upon opening said container, said cover to be manipulated while still in said container from said partially closed position to said closed position about a handle, and upon withdrawal of said cover from said container said flap springs into a position which isolates a control panel from a sterile field.

2. The assembly of claim 1 wherein said container includes a removable portion for opening said container.

3. The assembly of claim 1 wherein at least a portion of said container is constructed of a material which is permeable to a sterilant such that said cover can be sterilized while being carried by said container.

4. The assembly of claim 1 wherein said container includes an indented portion for maintaining said cover in a controlled partially closed position even after said container has been open.

5. The assembly of claim 1 wherein said means for holding includes a rib carried by said first half and a channel carried by said second half for receiving said rib in a locking engagement for holding said cover in said closed position.

* * * * *